United States Patent [19]

Colvard et al.

[11] Patent Number: 5,722,970
[45] Date of Patent: Mar. 3, 1998

[54] LASER SURGICAL METHOD USING TRANSPARENT PROBE

[75] Inventors: D. Michael Colvard, Pacific Palisades; Colette Cozean, El Toro; Varouj D. Amirkhanian, Glendale, all of Calif.

[73] Assignee: Premier Laser Systems, Inc., Irvine, Calif.

[21] Appl. No.: 391,612

[22] Filed: Feb. 21, 1995

Related U.S. Application Data

[63] Continuation of Ser. No. 280,280, Jul. 26, 1994, abandoned, which is a continuation of Ser. No. 74,996, Jun. 11, 1993, abandoned, which is a continuation of Ser. No. 680,815, Apr. 4, 1991, abandoned.

[51] Int. Cl.$^6$ ...................................................... A61N 5/06
[52] U.S. Cl. ............................ 606/3; 606/4; 606/13; 606/18
[58] Field of Search ........................ 606/3–6, 10, 15–18

[56] References Cited

U.S. PATENT DOCUMENTS

| | | | |
|---|---|---|---|
| 3,136,310 | 6/1964 | Meltzer | 128/634 |
| 3,348,547 | 10/1967 | Kavanagh et al. | 606/4 |
| 3,494,354 | 2/1970 | Yokota et al. | 128/6 |
| 3,865,113 | 2/1975 | Sharon et al. | 606/18 |
| 3,982,541 | 9/1976 | L'Esperance, Jr. | 606/4 |
| 3,996,935 | 12/1976 | Banko | 604/22 |
| 4,122,853 | 10/1978 | Smith | 606/11 |
| 4,233,493 | 11/1980 | Nath | 606/15 |
| 4,269,648 | 5/1981 | Dakss et al. | 350/96.18 |
| 4,313,431 | 2/1982 | Frank | 606/14 |
| 4,316,467 | 2/1982 | Muckerheide | 606/9 |
| 4,454,882 | 6/1984 | Takano | 128/395 |
| 4,538,608 | 9/1985 | L'Esperance, Jr. | 606/3 |
| 4,538,609 | 9/1985 | Tankenaka et al. | 606/19 |
| 4,551,129 | 11/1985 | Coleman et al. | 604/21 |
| 4,556,057 | 12/1985 | Hiruma et al. | 606/14 |
| 4,558,698 | 12/1985 | O'Dell | 128/395 |
| 4,576,177 | 3/1986 | Webster, Jr. | 606/7 |
| 4,583,539 | 4/1986 | Karlin et al. | 606/19 |
| 4,597,380 | 7/1986 | Raif et al. | 128/6 |
| 4,608,980 | 9/1986 | Aihara | 606/13 |
| 4,625,724 | 12/1986 | Suzuki et al. | 606/8 |
| 4,644,948 | 2/1987 | Lang et al. | 606/12 |
| 4,653,495 | 3/1987 | Nanaumi | 606/17 |
| 4,672,961 | 6/1987 | Davies | 606/7 |

(List continued on next page.)

FOREIGN PATENT DOCUMENTS

| | | |
|---|---|---|
| 0073617 | 8/1982 | European Pat. Off. . |
| 0214712 | 5/1986 | European Pat. Off. . |
| 0293126 | 5/1988 | European Pat. Off. . |
| 0368512 | 5/1990 | European Pat. Off. . |
| 0392951 | 10/1990 | European Pat. Off. . |
| 2828322 | 1/1980 | Germany . |
| 3816456 | 11/1989 | Germany . |
| 2182565 | 11/1985 | United Kingdom . |
| 8707133 | 5/1987 | WIPO . |
| 8900408 | 7/1988 | WIPO . |
| WO89/03202 | 4/1989 | WIPO . |

OTHER PUBLICATIONS

"Angioplasty with a Laser and Fiber optics at 2.94 μm" by Esterowitz et al SPIE Conference Notes Jan. 1986 Los Angeles CA.

*Primary Examiner*—David M. Shay
*Attorney, Agent, or Firm*—Knobbe, Martens, Olson & Bear, LLP

[57] ABSTRACT

Procedures using a laser surgical probe are disclosed in which laser energy can be directed at an angle relative to the longitudinal axis of the probe. In a preferred procedure, the laser probe is inserted into an internal portion of a mammal with a laser light beam being directed into the probe along a longitudinal axis. A reflecting surface on the probe reflects the laser light beam so that the beam exits the probe at an angle relative to the longitudinal axis, thereby directing the laser light onto tissue of the mammal. The tissue contacted by laser light can be viewed during the procedure by looking through the reflecting surface. A particularly preferred procedure comprises an anterior capsulotomy.

37 Claims, 9 Drawing Sheets

U.S. PATENT DOCUMENTS

| | | | |
|---|---|---|---|
| 4,718,417 | 1/1988 | Kittrell et al. | 606/7 |
| 4,740,047 | 4/1988 | Abe et al. | 606/17 |
| 4,744,360 | 5/1988 | Bath | 606/6 |
| 4,760,840 | 8/1988 | Fournier, Jr. et al. | 606/17 |
| 4,784,132 | 11/1988 | Fox et al. | 606/15 |
| 4,784,135 | 11/1988 | Blum et al. | 606/3 |
| 4,785,815 | 11/1988 | Cohen | 128/642 |
| 4,796,969 | 1/1989 | Fantone | 350/96.18 |
| 4,819,632 | 4/1989 | Davies | 606/15 |
| 4,825,865 | 5/1989 | Zelman | 606/6 |
| 4,830,453 | 5/1989 | Khoe | 350/96.18 |
| 4,846,154 | 7/1989 | MacAnally et al. | 128/6 |
| 4,846,172 | 7/1989 | Berlin | 606/4 |
| 4,848,336 | 7/1989 | Fox et al. | 606/7 |
| 4,849,859 | 7/1989 | Nagasawa | 606/17 |
| 4,917,084 | 4/1990 | Sinofsky | 606/7 |
| 4,983,009 | 1/1991 | Musk | 350/96.18 |
| 4,988,163 | 1/1991 | Cohen et al. | 606/15 |
| 5,041,121 | 8/1991 | Wondrazek et al. | 606/15 |
| 5,057,098 | 10/1991 | Zelman | 606/6 |
| 5,078,711 | 1/1992 | Kakami et al. | 606/16 |
| 5,084,043 | 1/1992 | Hertzmann et al. | 606/3 |
| 5,102,410 | 4/1992 | Dressel | 606/15 |
| 5,246,436 | 9/1993 | Rowe . | |

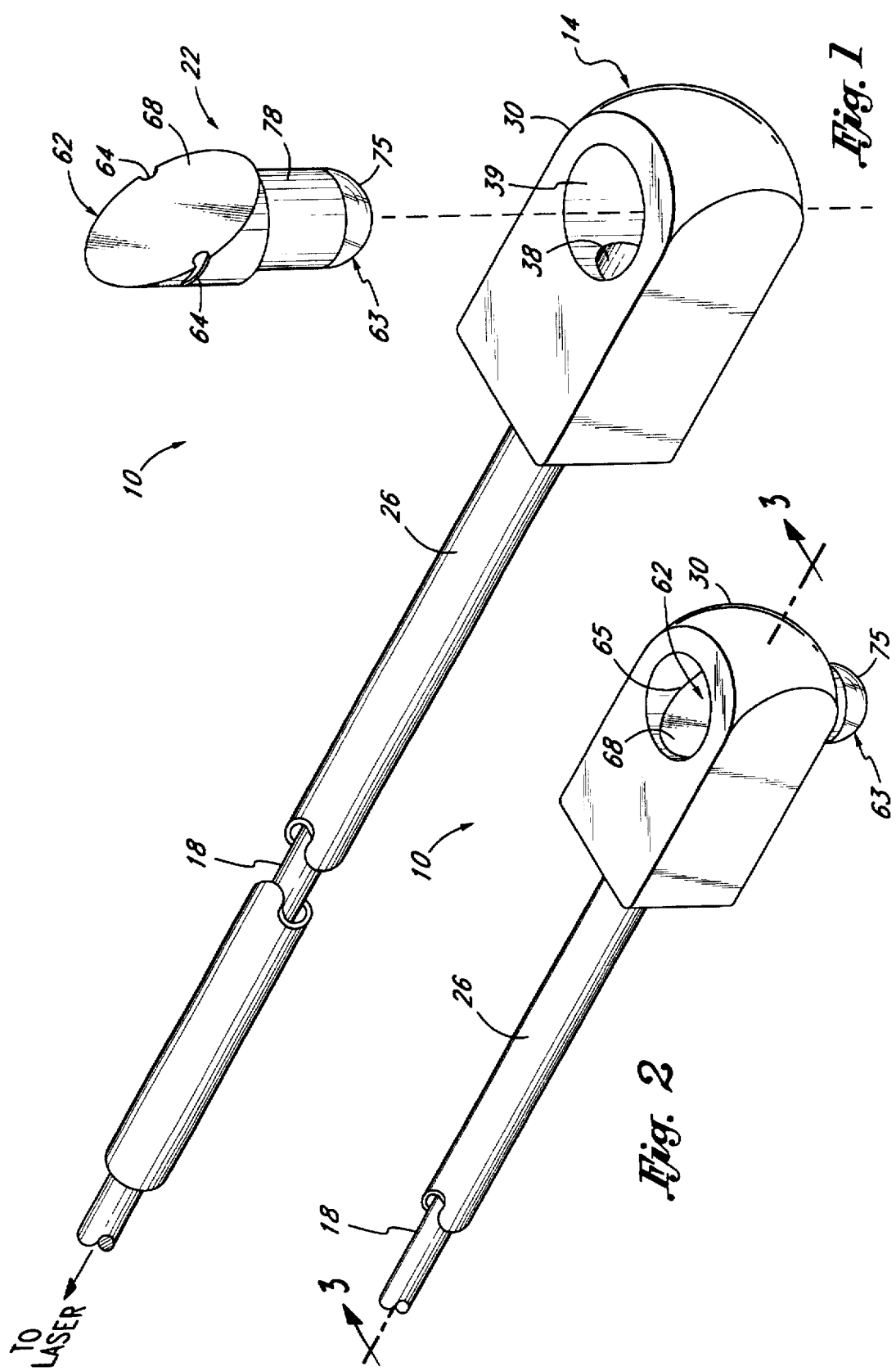

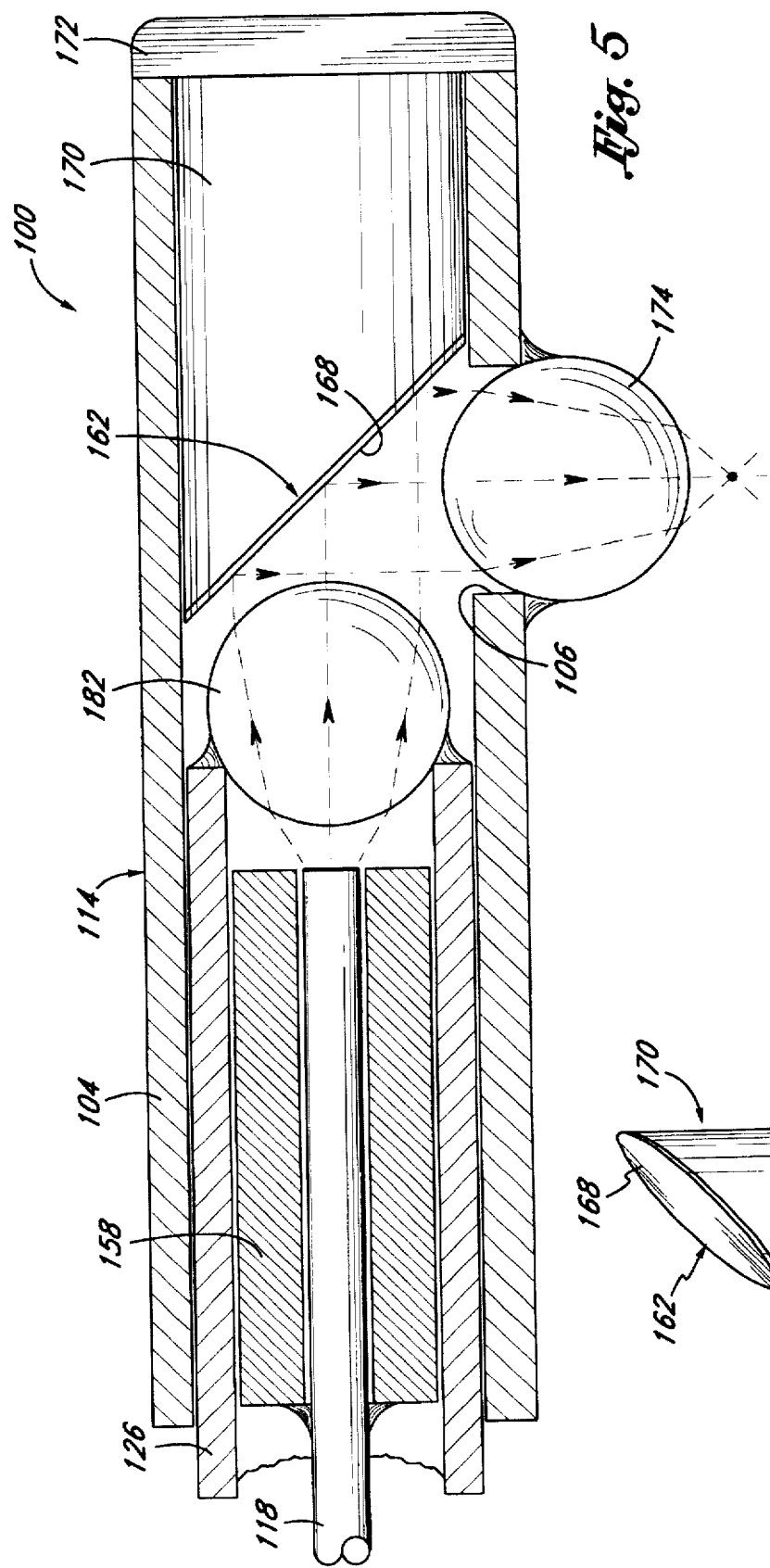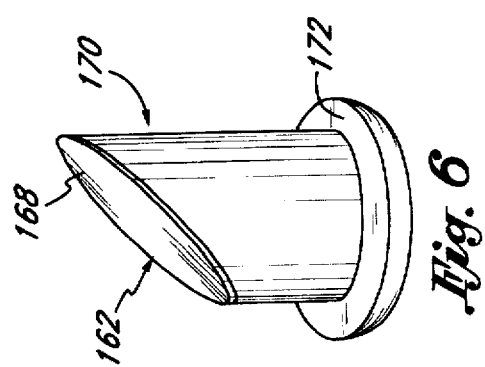

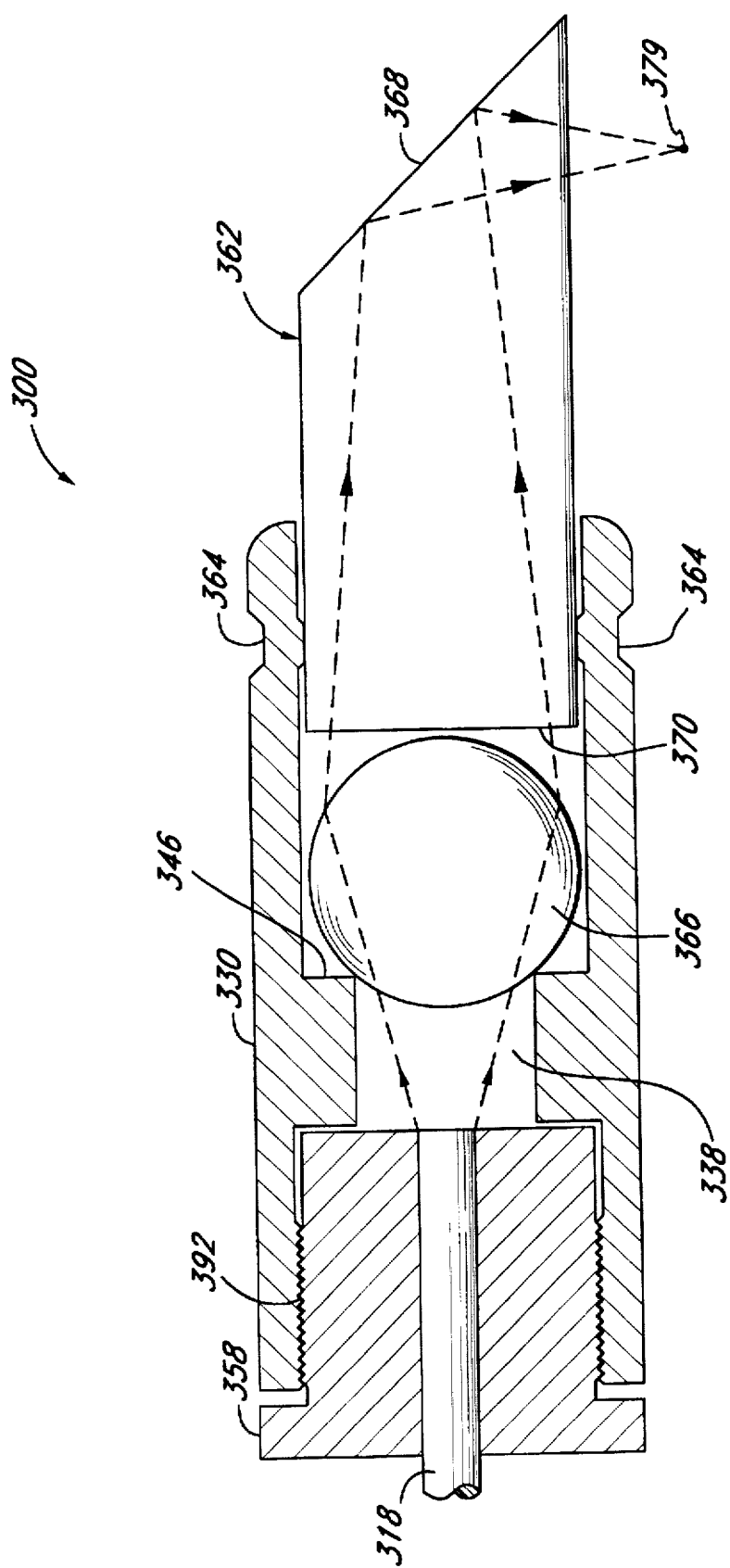

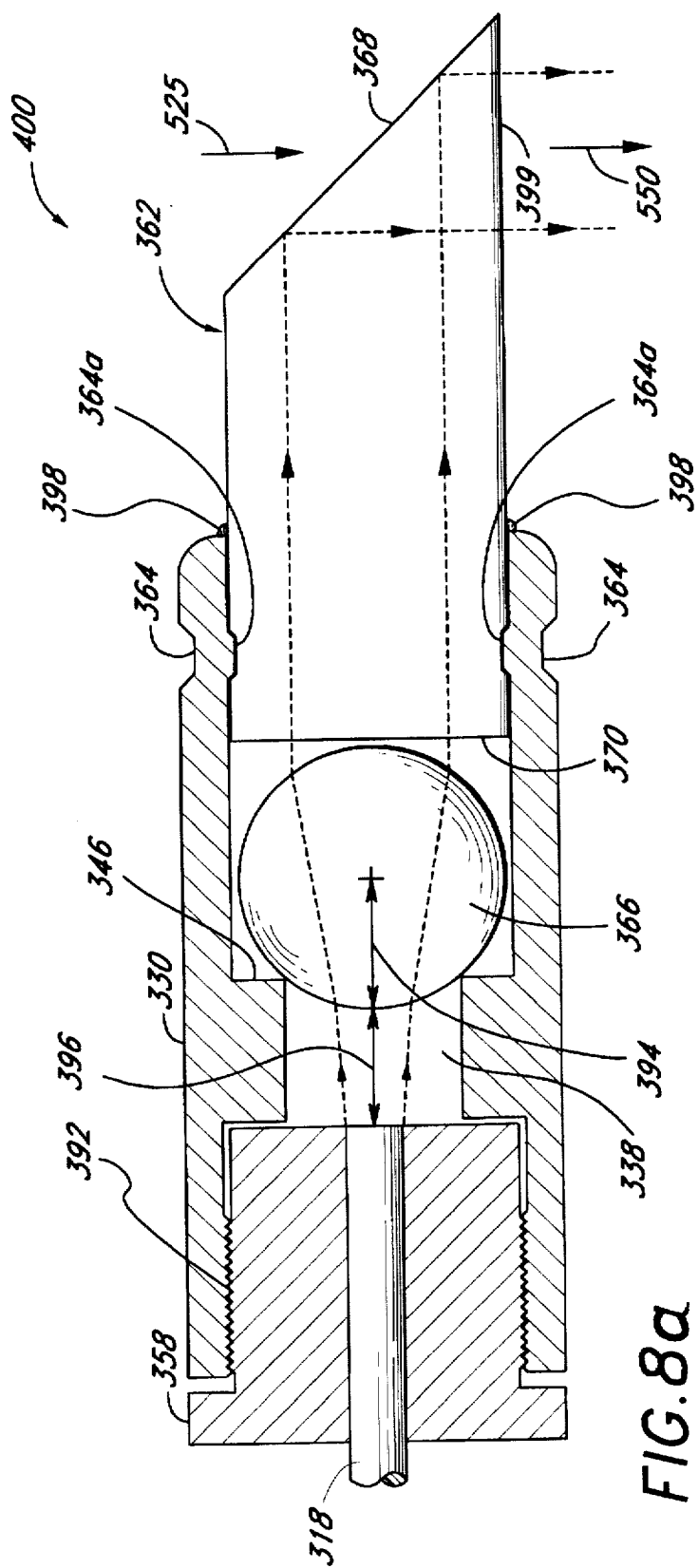
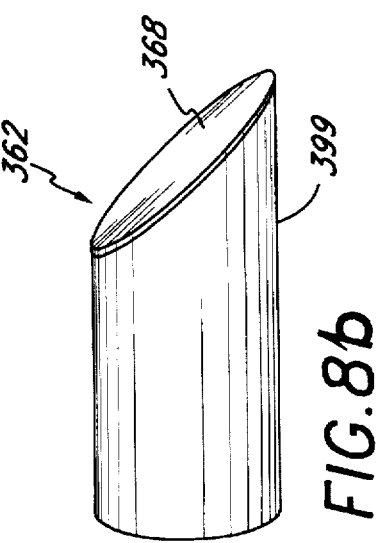
FIG.8a
FIG.8b

LASER SURGICAL METHOD USING TRANSPARENT PROBE

This application is a continuation of application Ser. No. 08/280,280, filed Jul. 26, 1994, abandoned, which is a continuation of Ser. No. 08/074,996, filed Jun. 11, 1993, abandoned, which is a continuation of Ser. No. 07/680,815, filed Apr. 4, 1991 (now abandoned).

BACKGROUND OF THE INVENTION

The present invention relates generally to the field of methods of use of laser surgical probes. More specifically, the present invention relates to use of laser surgical probes in which laser energy is output generally transversely relative to the laser energy input to the probe.

Surgical techniques making use of laser technology have been developed for a variety procedures. However, the usefulness of standard surgical laser probes is limited in many of these procedures, such as where the surgeon must operate within a tightly confined body cavity or lumen, or where the area requiring laser treatment is accessible only around a tight corner.

One type of surgery which has heretofore not employed laser technology involves anterior capsulotomies. In ophthalmic surgery, it is frequently necessary to perform these procedures in order to expose a portion of the lens underlying the anterior capsule. One example where anterior capsulotomies are useful is where a surgeon desires to remove all or part of the natural lens for replacement with an intraocular lens (IOL).

A number of techniques for anterior capsulotomy have been developed, many of which can be classified as "can opener" techniques, in which small scores are first placed around the region of the anterior capsule to be removed. These scores can be made by any of a variety of techniques, including the use of a needle, vibrating needle, or photodisruptive laser. After scoring, the surgeon tears between each of the scores to create a serrated capsular margin.

A disadvantage of can opener techniques for anterior capsulotomy is that unintended extension of the tears between scores can occur to form eccentric radial tears. These radial tears have been shown to result in asymmetric forces upon capsular contraction during healing. These asymmetric forces can result in decentration of an implanted IOL in the direction of the radial tear.

An improvement on can opener techniques for anterior capsulotomy is the continuous tear capsulotomy technique. This technique requires that the surgeon continuously tear the opening in the capsule. The technique results in a smooth non-serrated capsulotomy margin which is quite resistant to unplanned radial tears. However, the technique requires great skill, and the average ophthalmic surgeon is not likely to master the technique without extensive training and experience.

SUMMARY OF THE INVENTION

Briefly, the present invention provides a method of performing a surgical procedure on tissue in a mammal. The method comprises inserting a laser probe into an internal portion, such as the anterior chamber of the eye, of the mammal, directing a laser light beam into the probe along a longitudinal axis, redirecting the laser light beam so that the beam exits the probe along an output axis which is at an angle relative to the longitudinal axis of the probe and can be generally perpendicular to the longitudinal axis, and contacting tissue with the laser light such that the laser-tissue interaction can be seen through the probe. The method preferably also includes passing the visible light through the probe such that the visible light propagates along a viewing axis which is generally parallel to the output axis, and viewing the visible light after passing through the probe. In the preferred embodiment of this method, the visible light propagates towards the probe generally along the output axis. Preferably the laser light beam has a wavelength in an invisible portion of the optical spectrum and is at an absorbance peak of water. Light having a wavelength 2.94 μm is especially preferred. The redirecting step can be accomplished by reflecting the light beam at a surface of the probe through total internal reflection, with the surface being transparent to the visible light. The method can be used to form a smooth non-serrated capsulotomy margin with the laser light beam, followed by phacoemulsification or phacoablation of the lens underlying the anterior capsule. Advantageously, phacoemulsification can be performed using laser light from the probe. In certain aspects of this method, the tissue is irrigated with irrigation fluid, such as BSS, and fluid is aspirated from the region of the tissue. In a preferred embodiment of this method used in the eye, viscoelastic material, such as "Healon", is applied to the eye to maintain patency of the eye and hold tissues in position.

In accordance with another aspect of the present invention, there is provided a method of performing an anterior capsulotomy in the eye of a mammal. This method comprises inserting a laser probe into the anterior chamber of the eye, directing a laser light beam into the laser probe along an axis, redirecting the light beam at an angle relative to the axis, and forming a smooth non-serrated capsulotomy margin on the anterior capsule of the eye using the light beam. The probe used with this method preferably has a surface inclined at an angle to the axis, and this surface can be utilized to manipulate the portion of the anterior capsule within the margin for removal. The redirecting step can be accomplished by totally internally reflecting the light beam at this surface of the probe. While forming the margin, the margin can be viewed by looking through a transparent portion of the probe. The laser light beam used with this method is preferably of non-ultraviolet wavelength, more preferably also a wavelength at an absorbance peak of water. Such wavelengths can be produced by an Erbium:YAG laser. The light beam is also preferably provided as pulses at a frequency greater than 10 Hz, more preferably between 20 Hz and 30 Hz. The probe is preferably inserted through an incision in the sclera of the eye.

In still another aspect of this invention, a method of performing a surgical procedure using a laser probe is provided. This method comprises propagating invisible light to a reflecting surface for the probe, reflecting the invisible light, preferably by total internal reflection, from the surface such that the invisible light contacts tissue, propagating visible light from the tissue to the surface, passing at least some of the visible light through the surface, and viewing the visible light that has passed through the surface to determine the location where the invisible light contacts the tissue. The method preferably also includes delivering laser energy to said probe by a fluoride-based optical fiber and removing the probe tip to expose a bare end of the fiber and contacting tissue with laser light from the bare end. In an especially preferred embodiment, the reflecting surface forms a wedge on said probe, and the method additionally comprises using said wedge to manipulate tissue, such as separating planes of tissue. The propagation of invisible light can comprise cutting, phacoemulsification or phacoablation of tissue. The method can be performed during an ophthalmic procedure selected from the group consisting of corneal surgeries, keratectomy, keratoplastomy, glaucoma surgeries, filtration procedures, trabeculoplasty, iridectomies, iridotomies, cataract surgeries, capsulotomy, cataract extraction, vitreous surgeries, cutting of the vitreous bands, retinal surgery, removal of retinal membrane, and repair of retinal tears. The method can also be performed in a mammal during a non-ophthalmic procedure selected from the group consisting of surgery within a joint, surgery within a knee, procedures within long narrow passages, cardiovascular surgery and urethral surgery.

Further objects, features and other advantages of the present invention will become apparent from the ensuing detailed description, considered together with the appended drawings.

BRIEF DESCRIPTION OF THE DRAWINGS

FIG. 1 is a partially cut away, partially exploded, perspective view of one embodiment of a laser probe.

FIG. 2 is a perspective view of the assembly of the laser probe of FIG. 1.

FIG. 5 is an elevation view in partial cross-section, of an alternative embodiment, showing a schematic representation of the propagation path of laser light energy through the optical apparatus.

FIG. 6 is a perspective view of the rod used in the alternative embodiment of the laser probe of FIG. 5.

FIG. 8 is a cross-sectional view of still another embodiment of the laser probe.

FIG. 8a is a cross-sectional view of a modified laser probe of FIG. 8.

FIG. 8b is a perspective view of the rod used in the modified laser probe of FIG. 8a.

DETAILED DESCRIPTION OF THE PREFERRED EMBODIMENT

Figure 3:
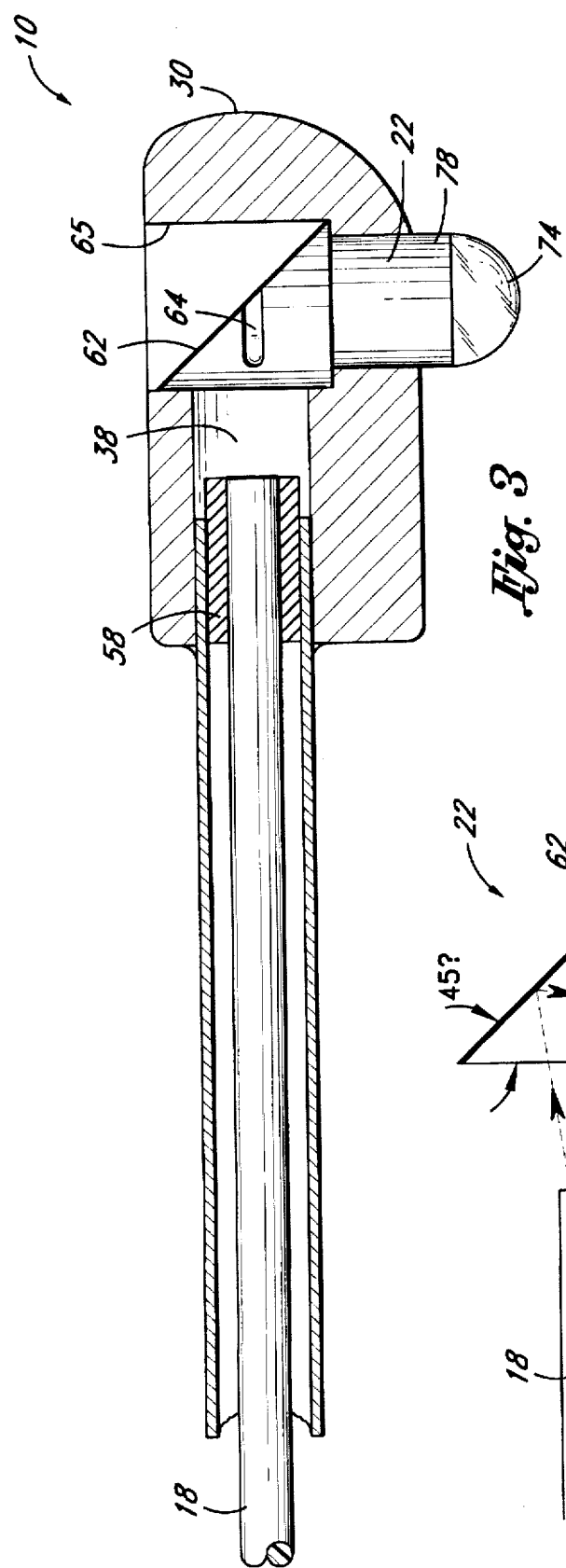
FIG. 3 is a partial cross-sectional view taken across line 3—3 in FIG. 2.

Referring now to the drawings in detail, wherein like reference numerals designate like elements throughout the several views thereof, there is shown generally at 10 in FIG. 1, a laser surgical probe for use in a preferred form of the present invention. The probe 10 comprises an elongate housing 14, an optical fiber 18 and an optical apparatus 22. The maximum diameter of the housing 14 is preferably no more than 2.5 mm.

Referring to FIGS. 1 and 2, the housing 14 comprises a fiber holder comprising an axially elongate hollow shaft, 26 and a head element 30 at the distal end of the shaft 26. The term "distal" designates the direction away from the laser light source, to which the probe is optically coupled. The term "proximal" shall mean the direction toward the laser light source 34. The term "longitudinal" shall be used to refer to a direction corresponding to an imaginary line running between proximal and distal ends. In FIG. 1, a portion of the shaft 26 is cut away to reveal the fiber 18 extending therethrough.

The head element 30 is contoured for smooth insertion into interior portions of a mammal. In order to allow the head element 30 to be withdrawn from the mammal without snagging, the head element is generally symmetrical about the axis for insertion. The head element 30 is also smoothly contoured at its proximal and distal ends in order to prevent snagging upon insertion or withdrawal of the probe 10. As an alternative, the entire probe 10 can be housed within an outer housing (not shown) which can be contoured for smooth insertion and withdrawal without snagging.

The head element 30 is preferably constructed from metal, such as aluminum or stainless steel. As best seen in FIG. 3, the head element 30 has a hollow space including a longitudinal tubular cavity 38 and a transverse tubular cavity 39, which allow for insertion of the optical fiber 18 and optical apparatus 22 therethrough, respectively. The transverse tubular cavity 39 extends through the head element 30 to form top and bottom openings in the head element 30. The optical apparatus 22 is positioned into the head element through the transverse tubular cavity 39. As will be explained in more detail below, the optical apparatus 22 is held in place by crimping of the head element material. The hollow shaft 26, which extends into a proximal end of the longitudinal tubular cavity 38, can, advantageously, be formed from stainless steel hypodermic tubing.

The longitudinal tubular cavity 38 extends from the proximal opening into the transverse tubular cavity. The diameter of the longitudinal cavity 38 is substantially the same as the outer diameter of the hollow shaft 26. The inner diameter of the shaft 26 is slightly larger than the outer diameter of the optical fiber 18. The optical fiber 18 is mounted in the hollow shaft 26.

Referring now to FIGS. 1–3, the head element 30 and hollow shaft 26 together form a housing 14 for the optical fiber 18 and optical apparatus 22. The head element 30 and hollow shaft 26 can be held together by any suitable method, such as by gluing with cyanoacrylate or by press fitting, brazing, soldering, or the like. Alternatively, the head element 30 and hollow shaft 26 can be formed as a unitary whole.

The optical fiber 18 is used to conduct a laser light beam towards the housing 14 and ultimately into the optical apparatus 22. Accordingly, the optical fiber 18 is optically connected at its proximal end to the laser light source. A preferred optical fiber 18 is a fluoride-based fiber, such as zirconium fluoride fiber having a numerical aperture of 0.2, which will produce an output cone of light having half angle of 11.5°. Aluminum fluoride fiber can also be provided. In the preferred embodiment, the fiber 18 is provided with a core and cladding of zirconium fluoride and a jacket of U.V. curable acrylate. Preferably, the fluoride-based fiber is in disposable, single-use form.

As best seen in FIG. 3, the optical fiber 18 is fixedly mounted in the tubular shaft 26 by a sleeve 58 comprising a tubular piece of material with an inner diameter slightly larger than the optical fiber 18 and an outer diameter slightly smaller than the inner diameter of the shaft 26. Alternatively, the fiber 18 can be bonded in place with glue or other materials.

In the preferred embodiment, the optical apparatus 22 (described hereinbelow) forms a single integral whole.

As described above, the optical apparatus 22 receives laser light from the optical fiber 18 along the longitudinal axis of the optical fiber. The optical apparatus 22 is formed from a dielectric material which is transparent to the beam of laser energy emanating from the optical fiber 18. For example, when an Erbium:YAG laser is used as the laser light source 34, which produces laser energy at 2.94 µm wavelength, sapphire is a preferred dielectric substance for formation of the optical apparatus 22. Advantageously, sapphire is readily machined into a variety of shapes useful as optical elements in the practice of the present invention.

The optical apparatus 22 is configured to redirect laser energy coming from the optical fiber 18 at an angle to the longitudinal axis of the optical fiber. As best seen in FIG. 1, the optical apparatus 22 comprises a diverter portion 62 and an intensifier portion 63. The diverter portion 62 reflects the laser energy output from the optical fiber 18. In the preferred embodiment, shown in FIGS. 1–3, the diverter portion 62 comprises a reflecting surface which is planar and is oriented at a predetermined angle relative to the propagation path of the light incident thereon. The reflecting surface is formed by a coating of reflective material which is 99.7% reflective at 2.94 µm ($R_{max}$).

As seen in FIGS. 1 and 3, in order to facilitate attachment to the head element 30, the optical apparatus 22 is provided with two notches 64. When the optical apparatus 22 is positioned at its proper position within the head element 30, the outer surfaces of the head element 30 can be crimped onto the notches 64, thereby fastening the optical apparatus 22 to the head element 30.

When the optical apparatus 22 is properly seated within the head element 30, a small cavity 65 remains above the optical apparatus 22. If desired, this cavity 65 can be filled or covered in order to protect the reflecting surface.

Figure 4:
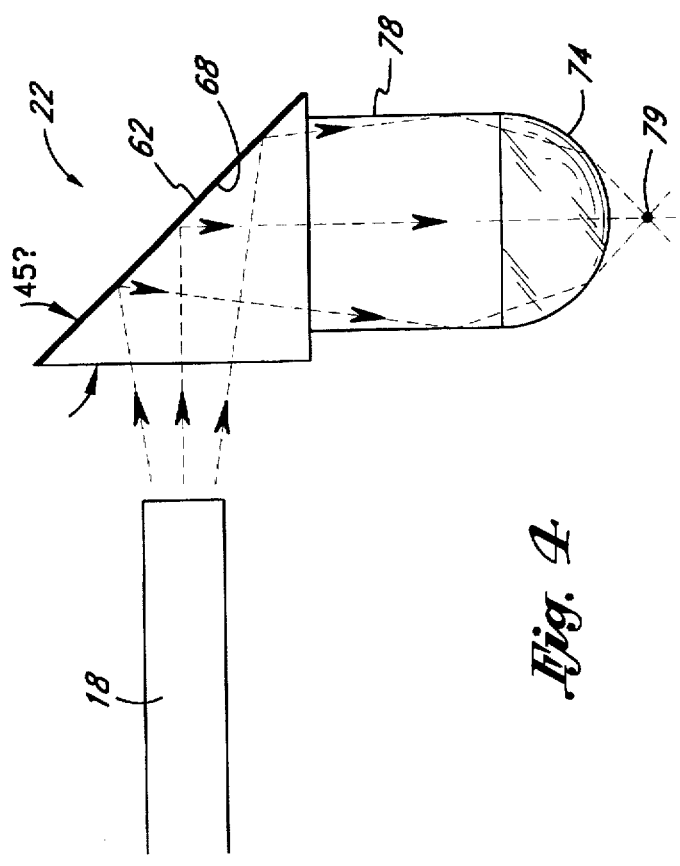
FIG. 4 is a schematic representation of the propagation path of laser light energy through the optical apparatus of the embodiment shown in FIGS. 1–3.

Referring now to FIG. 4, laser light energy entering the optical apparatus 22 from the optical fiber 18 will propagate through the optical element along its axis of egress from the fiber 18 until it reaches the diverter portion 62 of the apparatus 22. The diverter portion 62 is optically aligned and spaced from the optical fiber such that the output cone of laser light energy will cover the planar surface of the diverter portion 62 without significant amounts of laser energy loss. For the fiber used in this embodiment with a numerical aperture of 0.2, it is preferable that the distance 70 between the distal end of the fiber 18 and the proximal face of the optical element 22, measured along the longitudinal axis of the fiber, not exceed 0.02 inches. If the distance 70 exceeds this length, too much laser light energy may diverge outside of the reflective surface of the diverter portion 62.

Laser light energy reaching the diverter portion 62 is redirected at an angle which depends on the geometry of the diverting portion 62. For example, where the diverter portion 62 comprises a planar reflecting surface, such as that shown in FIGS. 1–4, the light will be redirected at an angle corresponding to the angle of incidence of the laser light energy on the reflecting surface 68. The reflecting surface 68 of the preferred embodiment is disposed at an angle of 45° relative to the longitudinal axis of the light output from the optical fiber. As seen in FIG. 4, this will produce an angle of divergence of the laser light energy of 90° relative to its initial axis of propagation. However, the reflecting surface 68 can be configured to provide any desired angle of divergence; particularly those angles greater than 30°, and more particularly greater than 45°.

The intensifier portion 63 of the optical apparatus 22 is disposed to receive the laser light energy that is redirected by the diverter portion 62. The intensifier portion 63 serves to concentrate the redirected light beam. Thus, the intensifier portion 63 can comprise a refracting surface, such as a focusing lens or a tapered tip, which produces the desired intensifying effect. In a preferred embodiment, the refracting surface is, advantageously, formed from the same dielectric material as the remainder of optical apparatus 22. In the embodiment shown, the refracting surface comprises a hemispherical lens 74.

The hemispherical lens 74 is disposed at the end of a cylindrical rod portion 78 of the optical apparatus 22 which serves as a waveguide portion. The waveguide portion 78 guides the redirected light reflecting from the reflecting surface 68 toward the refracting surface. The hemispherical lens 74 has a radius of curvature equal to the radius of the cylindrical rod portion 78.

The hemispherical lens 74 focuses laser light energy emanating from the shaft portion 78 to focal point 79. One feature of the refracting surface 74 is that it has a focal point 79 very close to the point of exit of laser light exiting therethrough. Preferably, this focal point is less than one millimeter from the refracting surface.

Referring now to FIG. 5, there is shown at 100, an alternative embodiment of the laser probe useful in the present invention. In this embodiment, an elongate housing 114 having a maximum diameter of 2.5 mm or less, the housing 114 comprises a head element 104 and a fiber holder 126, each of which is formed by an axially elongate hollow shaft, such as by hypodermic tubing. The outer diameter of the fiber holder 126 is approximately equal to the inner diameter of the head element 104, such that a distal end of the fiber holder 126 fits within a proximal end of the head element 104. The head element 104 has a circular opening 106 which provides access to the interior hollow portion of the housing 114 and also provides a route for egress of laser light energy.

In addition to the head element 104, the embodiment shown by FIG. 5 comprises an optical fiber 118. The optical fiber 118 may be the same as the optical fiber 18, described above in connection with FIGS. 1–3. The optical fiber 118 is connected to laser light source, such that laser light energy is transmitted through the optical fiber 118 in a longitudinal direction from proximal to distal. The optical fiber 118 is of smaller diameter than the inner diameter of the fiber holder 126, and thus a tubular optical fiber sleeve 158 is used to hold the optical fiber 118 in position within the housing 114. The fiber sleeve 158 has inner and outer diameters of a size sufficient to substantially fill the annular space between the fiber holder 126 and the optical fiber 118. The distal end of the optical fiber 118 is preferably co-terminous with the distal end of the fiber sleeve 158. The fiber sleeve 158 can be held to both the fiber holder 126 and the optical fiber 118 by interference fit. Alternatively, U.V. curable epoxy glue can be used to hold the sleeve 158.

In this alternative embodiment 100, the optical apparatus comprises separate components and is not unitary. A diverter portion 162 of the optical apparatus comprises a reflecting surface 168 formed by a reflective coating on the end of a sapphire rod 170. This rod 170 has a diameter slightly smaller than the inner diameter of the head element 104. Thus, the rod 170 can be inserted into the head element 104 in order to position the reflecting surface 168 such that the reflecting surface 168 directs laser light energy out of the head element 104 through the opening 106.

As best seen in FIG. 6, the rod 170 is provided with a disk 172 at its distal end which serves to prevent insertion of the rod 170 into the housing 104 further than the length of the rod 170. The rod 170 and disk 172 are preferably constructed from a single unitary piece of material. The disk 172 preferably has a diameter equal to the outer diameter of the head element 104, and is provided with curved corners at its distal end in order to create a smooth contour at the distal end of the probe 104, thereby allowing for smooth insertion and removal of the probe 100.

Preferably, an intensifier of the optical apparatus comprises a microball 174, having a spherical surface for refracting light. The microball 174 is preferably formed from dielectric material, such as sapphire, and can optionally be coated with an anti-reflective coating to increase optical transmission through the microball 174. Sapphire microballs 174 are, advantageously, easily fabricated, readily available and commonly used as couplers for fiber-optic cables. These microballs 174 are also available in sizes of 2.2 mm or less.

The microball 174 can be held on to the housing 114 by gluing it to the opening 106 with U.V. curable epoxy glue. Because the reflecting surface 168 is aligned to direct laser light energy from the optical fiber 118 toward the opening 106, placing the microball 174 within the opening 106 allows the microball 174 to perform its intensifying function on the light energy passing therethrough.

An optional feature of the optical apparatus of the various embodiments of laser probes useful in the present invention is a collimator. The collimator serves to substantially collimate the laser light energy emanating from the optical fiber prior to striking the diverting portion. In the alternative embodiment 100 shown by FIG. 5, the collimator of the optical apparatus comprises a collimating microball 182, similar to the microball 174 described above in connection with the intensifier.

The collimating microball 182 is positioned between the optical fiber 118 and the diverter 162, immediately distal (e.g., about 0.02 inches) of the distal end of the optical fiber. It is important that the distance between the microball 182 and the fiber 118 be relatively small so as to cause collimation rather than focusing. Thus, light emanating from the distal end of the optical fiber 118 is collimated before reaching the reflecting surface 168. Such collimation of the laser light energy serves to reduce or eliminate spherical aberrations of the light passing through the microball 174.

Figure 7:
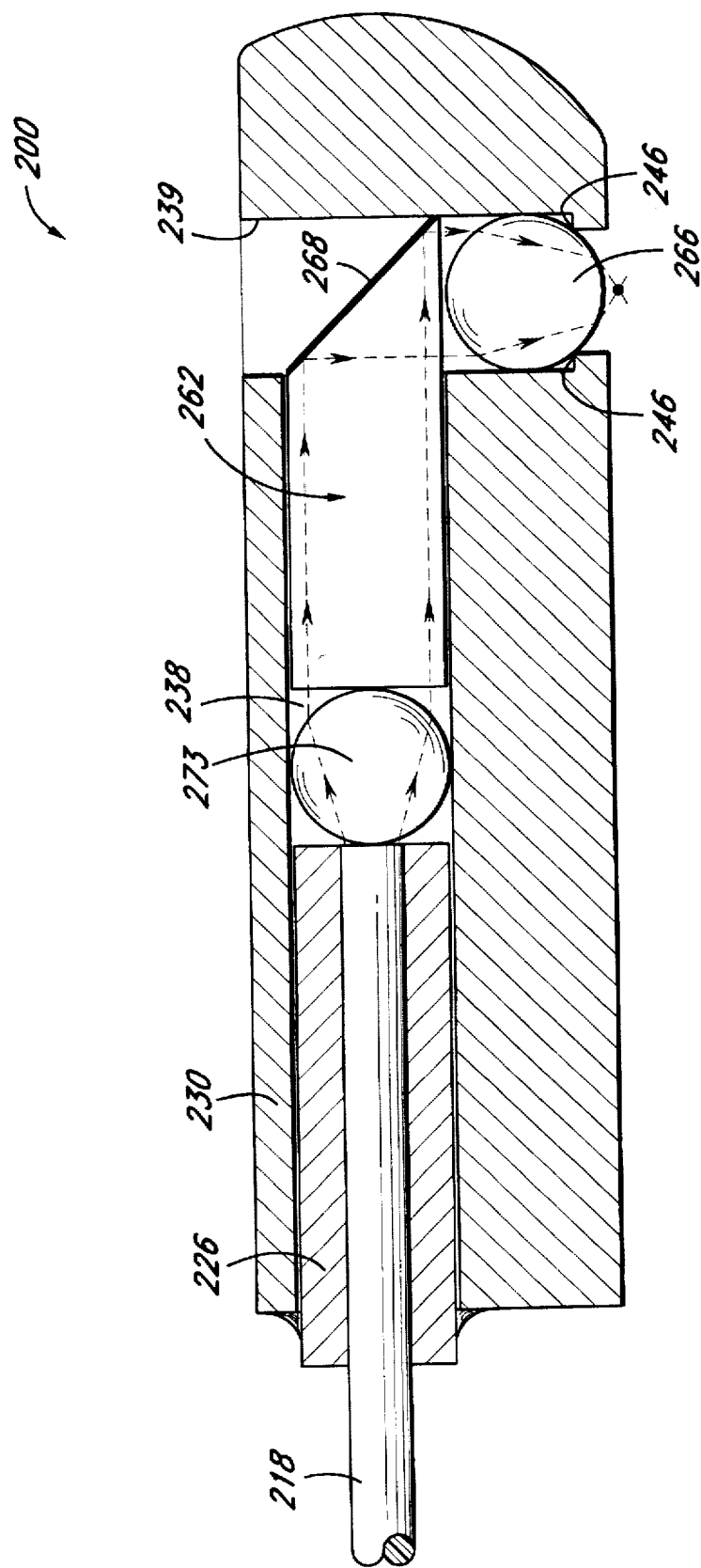
FIG. 7 is a partial cross-sectional view of another embodiment of the laser probe.

Referring now to FIG. 7, there is shown another embodiment of a laser surgical probe 200. The probe 200 comprises a fiber holder shaft 226 and a head element 230. The head element 230 is contoured for smooth insertion and withdrawal. The head element 230 has a longitudinal tubular cavity 238 and a transverse cavity 239. In this embodiment, the diameter of the transverse cavity 239 is constricted at the bottom relative to the remaining portion of the cavity 239, which is substantially tubular. Thus, a ledge 246 is formed within the transverse cavity 239.

The optical fiber 218 of this embodiment is fit into the head element 230 in a manner similar to that described above in connection with FIGS. 1–4. The optical apparatus of this embodiment comprises separate pieces, namely a collimator 273, a diverter 262 and an intensifier 266. As described in connection with FIGS. 5–6, the collimator 273 and the intensifier portion 266 comprise microballs, optionally coated with an anti-reflective coating.

The diverter 262 comprises a sapphire rod polished at a 45° angle at its distal end. The angled portion is coated with a reflective coating and forms a reflecting surface 268. The diameter of the rod is slightly smaller than the diameter of the longitudinal cavity 238 so that the diverter can be inserted therethrough.

The intensifier microball 266 rests on the ledge 246 and the diverter 266 is inserted through the longitudinal cavity 238 such that the microball 266 is held in the space between the ledge 246 and the diverter portion 268. The collimator microball 273, like the diverter portion 266, has a diameter slightly smaller than the diameter of the longitudinal cavity 238, and is inserted proximally of the diverter portion 266. Finally the optical fiber 218 within the shaft 226 is inserted into the longitudinal cavity 238. The shaft 226 is held to the proximal end of the head element 230 with U.V. curable glue. Thus, the diverter portion 266 and the collimator microball 273 are held within the portion of the longitudinal cavity 239 distal of the shaft 226. Preferably, there is substantially no space between the intensifier microball 266 and the diverter 262 or between the diverter 262 and the collimator microball 273.

Referring now to FIG. 8, there is shown still another embodiment of a laser surgical probe 300. The probe 300 comprises an optical fiber 318, a head element 330 and a fiber holder 358. The fiber holder 358 serves to provide a grip for the operator of the probe 300 and also serves as a sleeve for the optical fiber 318.

The head element 330 has a tubular longitudinal cavity 338 having proximal, middle and distal sections. The middle section has a constricted diameter relative to the proximal and distal sections of the cavity 338. The proximal section of the cavity 338 is threaded to accept a threaded portion 392 of the fiber holder 358.

The optical apparatus of the probe 300 comprises an intensifier 366 and a diverter 362. The intensifier comprises a spherical microball which is disposed in the distal section, and which rests on a ledge 346 formed by the constricted diameter of the middle section of the longitudinal cavity 338. The diverter 362 comprises a sapphire rod polished at a 45° angle at its distal end. The angled portion is coated with a reflective coating to form a reflecting surface 368. The diameter of the rod is slightly smaller than the diameter of the longitudinal cavity 338 so that the diverter can be inserted therethrough. The diverter 362 can extend beyond the distal end of the head element 330 as shown, or can be encased by the head element 330, with a hole at the point of emission of laser light energy. If the diverting portion extends beyond the distal end of the head element 330, the exposed sapphire can optionally be coated with a protective over-coat.

The distance between the distal end of the fiber 318 and the proximal portion of the intensifier microball 366, and the distance from the distal portion of the intensifier microball and the reflecting surface are selected so as to produce a focal point 379 a desired distance (e.g., less than 1 mm) from the bottom of the diverter 362. The distance from the intensifier microball 366 and diverter 362 can also be manipulated to provide the desired focal point 379. However, preferably, an input surface 370 of the diverter 362 is touching or almost touching the intensifier microball 366 in order to prevent axial movement of the microball 366.

The diverter 362 can be held in place by providing a notch 364 on the head element 330 and crimping the notch 364 to the diverter 362. If desired, the input surface 370 of the diverter 362 and the entire or proximal surface of the intensifier microball 366 may be coated with an anti-reflective coating to minimize reflection.

In use, the probe 300 is inserted into an internal portion of a mammal (e.g. an eye cavity) such that the rod 362 is surrounded by tissue and the portion of the rod extending from the housing is in contact with the tissue, although in the embodiment disclosed, the light beam is redirected by reflection, it will be understood that, by eliminating the reflective coating so that the light passes through the angled output face, redirection by refraction could be achieved. Such refraction is due to differences in refractive index at the angled output face. Redirection of the light beam by refraction may be similarly achieved by utilizing a bare rod, such as an optical fiber, and cleaving the end of the fiber of an angle (e.g. 45°) to cause the light output from the fiber to be deflected. Nevertheless, use of the reflective coating is preferred because a greater angle of deflection is possible.

Referring now to FIG. 8a, there is shown a probe 400 that is a modification of the laser probe 300 of FIG. 8. In this modified probe 400, the microball 366 is placed with its center 395 at its focal distance (f) from the distal end of the fiber 318. Placing the microball 366 in this position will achieve collimation of light incident thereon.

The focal distance (f) of a spherical lens can be calculated as f=n·r/2(n−1), where n is the index of refraction and R is the radius 394 of the lens. For the preferred embodiment having a 1.5 mm diameter spherical sapphire lens and using a laser producing light energy of wavelength 2.94 µm, the index of refraction of the lens is 1.72. Thus, for this preferred embodiment, f=1.72 (0.75)/2(1.72−1)=0.896 µm.

For a properly placed microball 366 achieving collimation of light from the fiber 318, the focal distance (f) will be equal to the length of the radius (R) 394 of the microball 366 plus the gap (g) 396 between the microball 366 and the distal end of the fiber 318, i.e. f=g+R. Thus, in the preferred embodiment described above, the proper gap 396 can be calculated as g=f−R=0.896 mm−0.75 mm=0.146 mm.

In use of the probe 400, the collimated light travels along the longitudinal axis of the probe 400 until meeting the reflecting surface 368. The reflecting surface 368 diverts the light in a direction along an output axis 550 which is at an angle relative to the longitudinal axis of the probe 400. For many procedures, such as an anterior capsulotomy, the preferred angle of the output axis is perpendicular to the longitudinal axis of the probe 400. For other procedures, such as certain procedures in the treatment of glaucoma, angles greater or less than 90° are preferred.

In the modified laser probe 400, the reflecting surface 368 is transparent and requires no reflective coating. Rather, reflection occurs due to the total internal reflection achieved from the differences in the indices of refraction between the material of the rod 362 and the material surrounding the probe 400. In the preferred embodiment, the rod 362 is sapphire, having an index of refraction (n) of 1.7 with light produced by the Erbium:YAG laser having a wavelength of 2.94 µm.

The critical angle ($\theta_c$) of the reflecting surface 368 required to achieve total internal reflection can be determined according to Snell's law, which can be stated as follows: $n_1 \sin\theta_1 = n_2 \sin\theta_2$. As stated above, in the preferred embodiment, $n_1$=1.7. When the probe is used in air, $n_2$=1.0. For total internal reflection $\theta_2$=90°. Thus, $\theta_c$ for the rod of the preferred embodiment can be calculated from Snell's law as follows: $1.0\sin\theta_c=1.72\sin 90°$. Accordingly, $\theta_c$=35.5°. This means that total internal reflection will be achieved as long as the reflecting surface 368 is at an angle greater than or equal to 35.5° with respect to the collimated light incident thereon.

The probe 400 functions to reflect light in substantially the same manner in a fluid environment (e.g. $H_2O$) as in air because the refractive index difference between the fluid and the sapphire rod 362 is sufficiently great to cause total internal reflection to occur at the surface 368.

As best seen in FIG. 8b, in the preferred embodiment, the rod 362 comprises a sapphire rod of circular cross section which is polished at a 45° angle at its distal end to form the reflecting surface 368. When the modified laser probe 400 of this preferred embodiment is used in air and not in contact with tissue, the curved bottom output surface 399 of the rod 362 acts as a cylindrical lens to focus the collimated light into a more linear form. However, when the laser probe 400 is used in a fluid environment (e.g. $H_2O$) or in contact with tissue, the lens action of the output surface 399 tends to be negated due to the higher index of refraction of the fluid and/or due to the contact with tissue at the cylindrical surface. Thus, when the modified laser probe 400 is used in internal portions of a mammalian body, such as in the eye, the light exiting the probe will be in a roughly tubular form. Advantageously, where total internal reflection is used to reflect the light within the probe 400 without the use of a reflective coating, the probe is transparent to allow the user of the probe 400 to view the point of contact of the laser light energy on tissues or other materials. This is particularly advantageous in surgeries, such as anterior capsulotomies, where the probe would otherwise obscure the contact point of the light energy. Another advantage of the probe 400 of FIG. 8a is that the wedge-shaped end of the probe, formed by the angled reflecting surface 368, can be used as a tool to physically manipulate tissues without the need to insert an additional tool.

Although the 2.94 µm wavelength light energy of the Erbium:YAG laser is not visible to the human eye, the point of contact can generally be seen due to the energy released by the tissues after coming into contact with the laser energy from the probe 400. The tissue absorbs the collimated infra-red light emitted from the probe along the output axis 550 and causes a laser-tissue interaction to occur. This interaction generally results in the release of light of a wide spectrum, including visible light, at many different angles. Thus, much of the light released by laser-tissue interaction will strike the reflecting surface 368 at an angle less than the critical angle. Even without release of significant quantities of light by laser-tissue interaction, the interaction can be seen by the formation of an incision or other effect on the tissue by the laser. Accordingly, the operator of the probe can look through the transparent reflecting surface 368 along a viewing axis 525 to view the visible light from the tissue during operation of the probe 400. The viewing axis is generally perpendicular to the longitudinal axis of the probe 400.

In the preferred embodiment of the laser probe 400, all surfaces are polished with optical grade (e.g. 0.3 µm) polish, including the distal end of the fiber 318. Without this polishing, specular reflections can occur which result in a dispersal of the energy passing through the probe 400.

As discussed above, all surfaces should be generally smooth to prevent snagging during insertion or removal of the probe 400. Thus, in the preferred embodiment, one or more notches 364a are provided on the rod 362 which will allow the rod 362 to be held to the head element 330 by crimping of the head element at the position of each notch 364a.

The laser probe 400 can advantageously be configured to supply irrigation fluid or vacuum for aspiration as frequently employed with known phacoemulsification devices. Alternatively, irrigation and/or aspiration can be supplied from separate devices inserted into the region of use of the probe 400.

In the preferred embodiment, it is important that fluid not enter the longitudinal cavity 338 of the head element 330 because the lenses are configured for use with air with an index of refraction of 1.0 in these spaces. The entry of fluid with a much higher index of refraction into the cavity 338 would prevent collimation of the light energy emanating from the fiber 318. Thus, a sealant 398, such as epoxy glue is preferably provided at the junction between the rod 362 and the head element 330, to prevent entry of fluid into the cavity 338.

Figure 9:
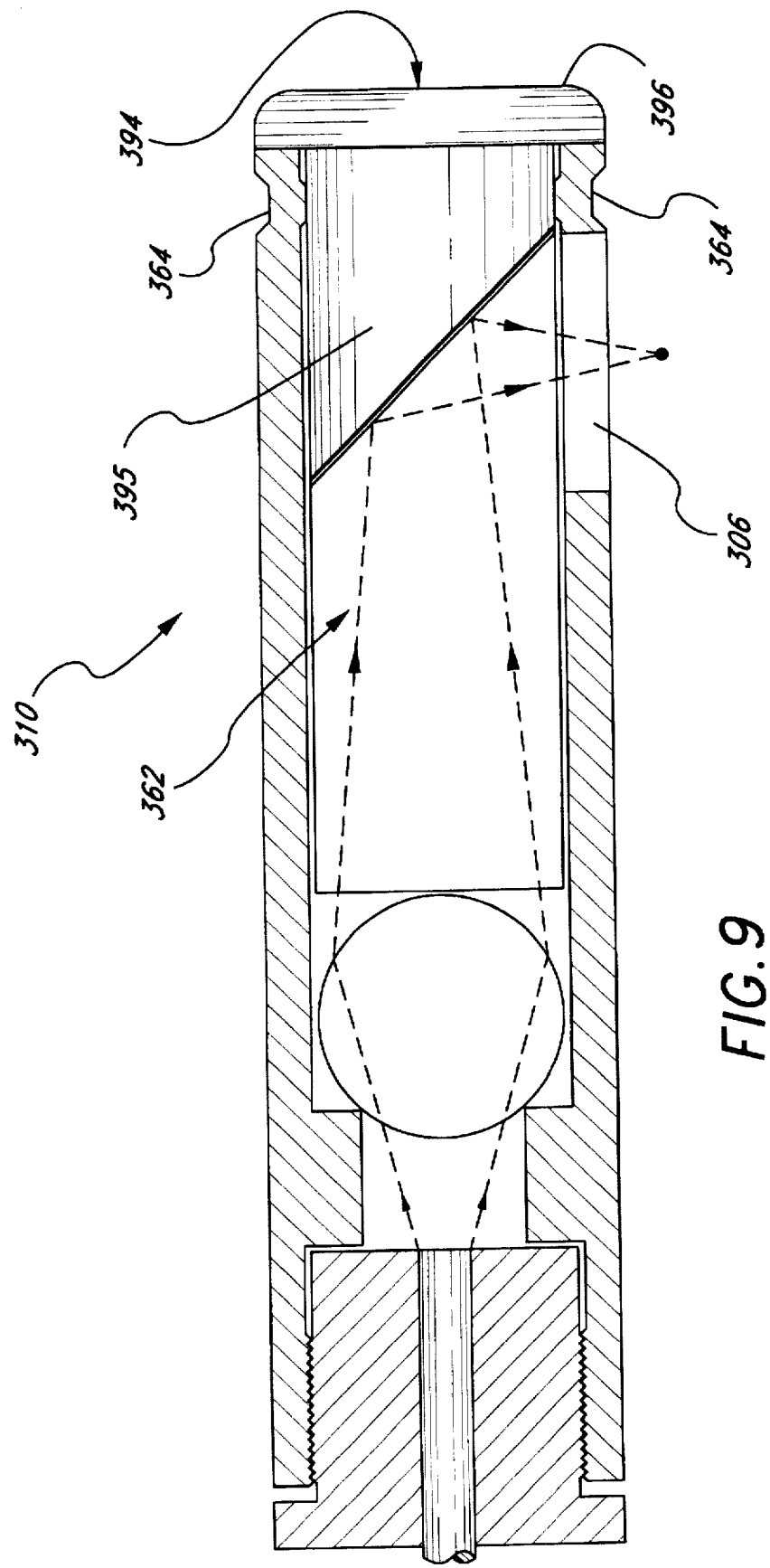
FIG. 9 is a partial cross-sectional view of a variant of the laser probe of FIG. 8.

Referring now to FIG. 9, there is shown a variant 310 of the laser probe 300 of FIG. 8. In this variant, the head element 330 is elongated to extend beyond the diverter 362, and comprises an opening 306 to allow laser light energy to be emitted outside the head element 330 after it has been diverted by the diverter 362. In the variant 310, a cap 394 is inserted at the end of the head element 330. The cap 394, comprises a rod portion 395 and a flange portion 396. The diameter of the rod portion 395 is slightly smaller than the diameter of the longitudinal cavity 338 so that the rod portion 395 can be inserted therethrough. The rod portion 395 is cut an angle which will complement the angle of end the diverter rod 362 to substantially completely fill the longitudinal cavity 338 at its end. Thus, if the diverter rod 362 is cut at a 45° angle, the rod portion 395 will also be cut at a 45° angle. The length of the rod portion is selected to substantially completely fill the end of the longitudinal cavity 338. The flange portion 396 provides a smooth surface for easy insertion and withdrawal of the variant laser probe 310. The cap 394 is held in place by crimping the notches 364 to the cap 394, thereby also preventing axial movement of the diverter rod 362.

The laser probes 10, 100, 200, 300, 310, 400 are useful in a wide variety of surgical procedures, including procedures such as described by Berlin in U.S. Pat. No. 4,846,172. The use of the laser probes 10, 100, 200, 300, 310, 400 is especially advantageous in procedures where it is desired to operate a laser probe within a tightly confined space, such as within bodily tissues or a tightly confined body cavity or lumen. The probe allows a surgeon to direct laser energy from the side of the probe, thereby allowing laser energy to be directed around tight corners.

Particular examples of procedures in which the probe can be applied in a mammal include ophthalmic procedures of many types. In this regard, the probe can be used for cutting, phacoemulsification and phacoablation. These and other techniques using the probe are believed to be especially useful in corneal surgeries, such as keratectomy or keratoplastomy, in glaucoma surgeries, such as filtration procedures, trabeculoplasty, iridectomies or iridotomies, in cataract surgeries such as capsulotomy or cataract extraction, in vitreous surgeries such as cutting of the vitreous bands, and in retinal surgery such as removal of retinal membrane or repair of retinal tears. Non-ophthalmic procedures on a mammal in which the probe is believed to be useful include surgery within a joint, such as a knee, and procedures within long narrow passages, such as can be found within the cardiovascular system and the urethra.

The intensity of the light input to the probe is regulated, depending on the procedure, to provide sufficient intensity to achieve the desired result such as cutting, welding, vaporization or coagulation of biotic material (e.g. tissue). Where smooth cutting is desired, the frequency of the pulse should be in excess of 5 Hz, preferably 10 Hz–30 Hz or more. It is also preferable to use a laser light source with a relatively low energy threshold in order to provide smooth cutting. Preferably the energy threshold is 5–10 mJ for cutting of the anterior capsule of the eye. Thus, for smooth cutting energy levels of 30 mJ per pulse are less are preferred, with energy levels just above the energy threshold of 5–10 mJ/pulse being especially preferred.

Figure 10:
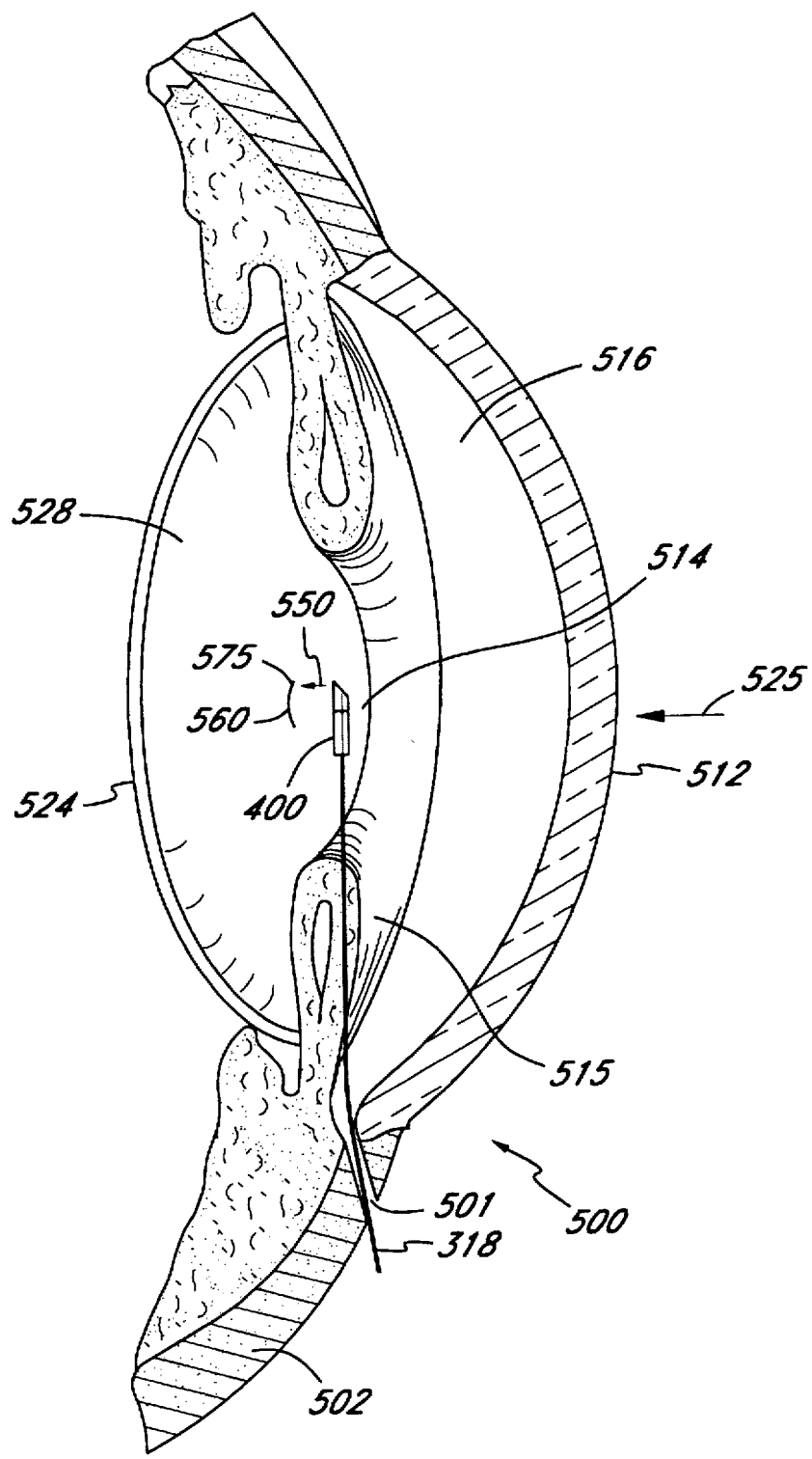
FIG. 10 is a partial cross-sectional view in perspective of an eye of a mammal showing the laser probe in use during an anterior capsulotomy procedure.

As stated above, one procedure in which the probe is particularly useful is in anterior capsulotomy of the eye. With reference to FIG. 10, in which a cross section of an eye 510 is shown, a small roughly circular incision 501 through one side of the sclera 502 of the eye 500 is first made into the anterior chamber 516. This incision is roughly 2.0–3.5 mm in diameter. As discussed above, the probe is preferably contained within a housing having a diameter of 2.5 mm or less. This is advantageous in anterior capsulotomies and other procedures within the eye because larger probes would require a larger incision. Moreover, the use of large probes also increases the risk that the probe will come into contact the cornea 512, iris 515 or other delicate tissues within the eye 500, resulting in damage to these tissues.

In order to maintain the patency of the anterior chamber 516 during the procedure and to hold other tissues in position, the chamber 516 can be filled with a viscoelastic material, such as "Healon". The viscoelastic material will also hold tissues in position within the eye during the procedure. Alternatively, irrigation fluid, such as balanced salt solution (BSS) can be continuously infused to maintain patency of the chamber 516.

The probe 400 or other laser probe can be inserted into the incision 501 along with the fiber 318 transmitting laser energy thereto. The probe is then manipulated to cut a circular incision (shown partially formed at 560 in FIG. 10) around a portion of the anterior capsule 524 adjacent the lens. As will be discussed in more detail below, the laser probe 400 advantageously allows the operator to view the energy released from the surface of the capsule as laser light energy is applied.

A variety of laser light sources may be used in the procedure. However, it is preferred that the laser light source provide a smooth, non-serrated capsular margin, in order to enable a surgeon to make a clean circular cut on the anterior capsule. A percussive device would not be appropriate, which would punch ragged holes in the capsule. Thus, the frequency of the laser pulse should be in excess of 10 Hz, preferably 20 Hz–30 Hz or more, as discussed above.

Preferably, a laser light source producing light at a wavelength readily absorbed by water is provided. Use of wavelengths that are absorbed readily by water is useful for ablation of tissues. Also, use of such wavelengths serves to prevent unwanted transmission and scatter of laser energy to adjacent or underlying tissues, resulting in minimal thermal damage to these tissues. It is also preferred that the laser light be deliverable by an optical fiber to allow the user of the probe to deliver the laser light energy by hand. Hand delivery is important for allowing delicate manipulations within the eye and other tightly confined tissues.

Thus, a preferred laser light source is an Erbium:YAG laser which produces laser light energy of wavelength 2.94 μm, a wavelength at which water has an absorbance peak. Thus, one preferred wavelength range for the light energy for use with the probe 400 is the range from 2.8 μm to 3.0 μm. The Erbium:YAG laser provides several additional advantages. First, the energy is non-ultraviolet, thereby allowing work in the eye with increased safety, obviating the need to use blocking elements or device to prevent retinal toxicity. Second, the Erbium:YAG light source can also be configured to provide the pulse frequency greater than 10 Hz needed to provide smooth cutting. Third, the high absorbance by water makes the laser safer, more controllable, and more precise. Fourth, the laser has a low thermal component, allowing for precise spatial confinement of energy deposition and reducing thermal damage and charring of intraocular tissues. Finally, the Erbium:YAG laser is relatively inexpensive to manufacture and maintain compared to certain other lasers.

Laser light sources which produce energy at other non-ultraviolet absorbance peaks of water, such as 2.1 μm, and are deliverable by optical fiber provide advantages similar to those provided by the Erbium:YAG laser. Thus, another preferred laser light source is the Holmium:YAG laser which is hand deliverable and provides laser light energy within the range of 1.9 μm to 2.2 μm.

Delivering laser light energy by fiber 318 provides the additional advantage of allowing use of the bare fiber through removal of the probe tip. Thus, in the preferred embodiment, the probe tip is removable by hand to expose the distal end of the fiber 318, thereby enabling use of the bare fiber end from the same hand held instrument. Use of the bare fiber is advantageous in many procedures, such as the excision of a vitreous band within the eye of a mammal.

As seen in FIG. 10, laser light energy exits the probe along its output axis 550 to contact the tissue at a point of contact 575. In order to view the point of contact 575 through the viewing axis 525, the surgeon or operator of the probe must look through the probe 400. Advantageously, when the incision in the capsule 524 is made with a transparent laser probe having an uncoated, transparent reflecting surface 368, such as the probe 400 of FIG. 8a, the surgeon can look through the surface 368 of the probe 400 to view the incision 560 at the point of contact 575 while the incision 560 is being cut. Thus, in order to view the point of contact 575 the surgeon can look through the cornea 512, pupil 514 and the transparent reflecting surface 368 along the viewing axis 525. Preferably, the viewing axis 525 is generally parallel to the output axis 550, and in an especially preferred embodiment, the viewing axis 525 is collinear with the output axis 550. In many procedures, including anterior capsulotomies, it is desirable to provide a microscope (not shown) for viewing the point of contact under magnification.

Being able to view the point of contact 575 while the incision 560 is being cut, advantageously allows the surgeon to avoid sensitive areas and to more easily control the size and shape of the incision 560. Advantageously, viewing the point of contact 575 also allows the surgeon to more readily cut a smooth incision 560. Thus, decentration and other problems associated with less smooth incisions are avoided.

After the smooth incision 560 has been made on the anterior capsule, the cutout portion of the anterior capsule 524 inside the incision 560 is removed to expose the underlying lens 528. If necessary, this cut out portion of the lens 528 can be manipulated using the wedge formed by the reflecting surface 368 on the probe 400. Advantageously, this wedge can be used to manipulate other tissues inside the eye or elsewhere as well. The wedge has also been found to be advantageous in readily allowing the user of the probe to separate planes of tissue, such as in separating fascia from muscle or separating the anterior capsule 524 from the underlying lens 528 within the eye 500.

Figure 11:
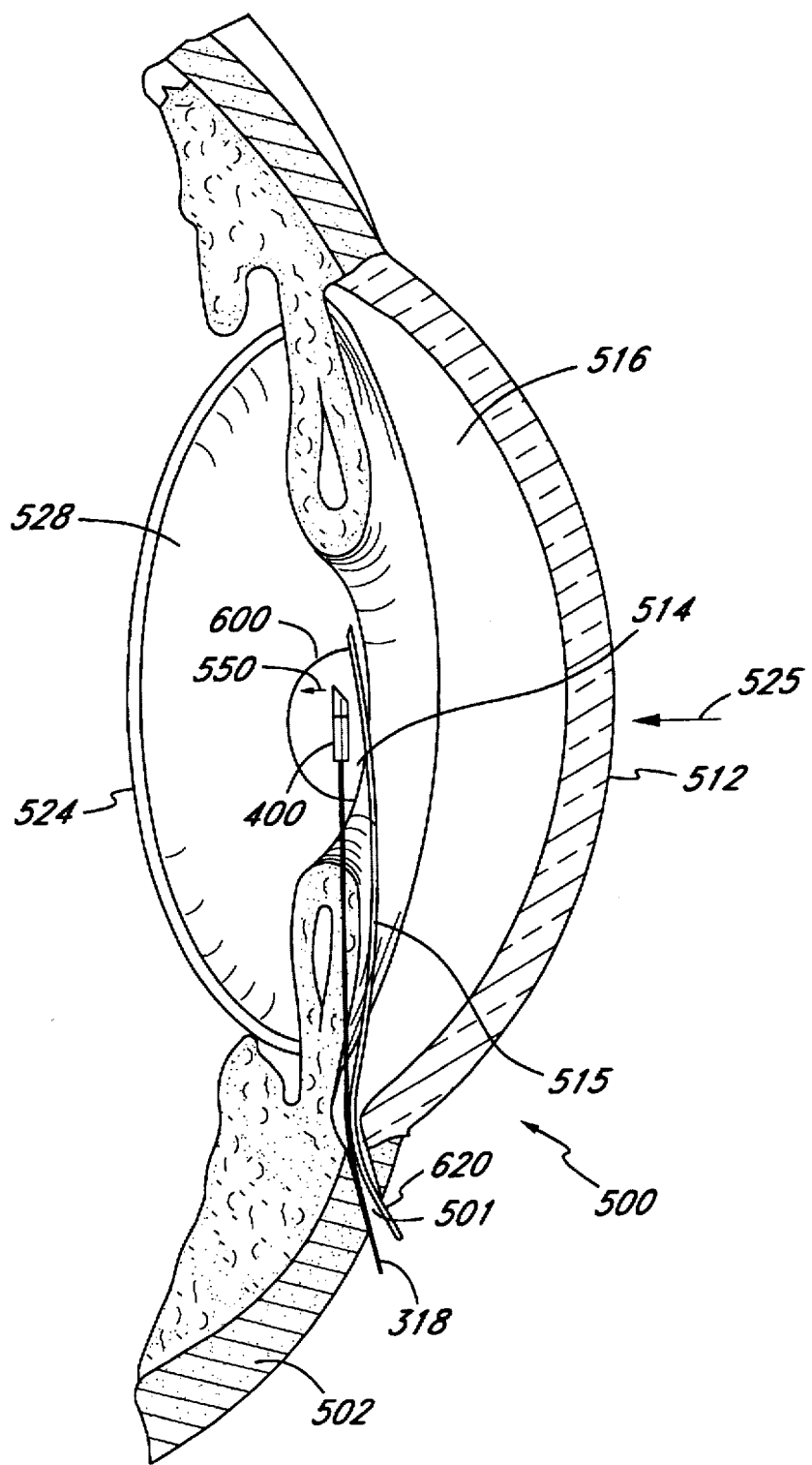
FIG. 11 is a partial cross-sectional view in perspective of an eye of a mammal showing the laser probe in use during a phacoemulsification procedure with irrigation.

For insertion of an intraocular lens (IOL), the lens 528 can first be emulsified in a manner known to those of skill in the art, such as through phacoemulsification using an ultrasonic device. Advantageously, as shown in FIG. 11, the laser probe 400 can also be used for emulsification, preferably using a higher energy level than used for incision, e.g. 100 mJ/pulse. The probe 400 can be used to deliver light energy to emulsify the lens within the completed capsular margin 600. There is less need for high frequency of laser light energy pulses during emulsification, thus frequencies of 5 Hz or less can be used. During emulsification, the high energy laser light energy exits the probe along output axis 550, and the lens tissue within the margin 600 contacted by the laser light can be viewed through the probe 400 as discussed above.

The emulsified lens material can advantageously be removed using irrigation and aspiration supplied along with the probe 400. The use of irrigation means 620 is shown in FIG. 11. The use of irrigation means 620 and aspiration means for this purpose as part of a laser probe is well known, and has been described, for example in U.S. Pat. Nos. 4,846,172 and 4,784,132, the disclosures of which are hereby incorporated by reference. Irrigation and/or aspiration can also be supplied as separate components, as is well known to those of skill in the art. After emulsification of the lens 528, the eye 500 is ready for implantation of the IOL.

It will be appreciated that certain structural variations may suggest themselves to those skilled in the art. The foregoing detailed description is to be clearly understood as given by way of illustration, the spirit and scope of this invention being limited solely by the appended claims.

What is claimed is:

1. A method of performing a surgical procedure, using a laser probe which comprises a member having a longitudinal axis and a reflecting surface, comprising the steps of:

grasping the probe with a hand of a user and positioning the probe for surgery;

propagating invisible laser light through said probe;

outputting invisible laser light from said probe along an output path which extends in a direction transverse to said longitudinal axis, the step of outputting comprising reflecting the invisible laser light from said reflecting surface on said member and then passing the reflected laser light through an output surface on said member;

surgically altering tissue by contacting the tissue with said invisible light at a point of contact;

moving said point of contact relative to said tissue;

visualizing the point of contact using a method comprising:

propagating visible light from said point of contact to said probe in said transverse direction substantially along said output path;

passing at least some of said visible light completely through said probe in said transverse direction to provide a viewing beam which exits said probe along a viewing axis transverse to the longitudinal axis, the step of passing further comprising passing the visible light first through the output surface and then through the reflecting surface; and viewing said visible light that has passed along said viewing axis through said probe to determine the location where said invisible light contacts said tissue.

2. A method of performing a surgical procedure on an eye, comprising:

inserting a laser probe into an anterior chamber of said eye;

delivering a laser light beam from a laser to said probe;

directing said laser light beam into said probe along a longitudinal axis;

redirecting said laser light beam inside said anterior chamber so that said beam exits said probe along an output axis at an angle relative to said longitudinal axis;

contacting an anterior lens capsule in said eye with said laser light at a point of contact;

moving said point of contact along a capsulotomy margin to cut an opening in the anterior capsule and thereby provide a cut portion of said capsule interior to said margin; and moving the cut portion of the anterior capsule so as to expose the lens.

3. The method of claim 2, wherein the output axis is generally perpendicular to said longitudinal axis.

4. The method of claim 2, wherein said laser light beam is of light having a wavelength at an absorbance peak of water.

5. The method of claim 1, additionally comprising aspirating fluid in the region of said tissue.

6. The method of claim 2, additionally comprising passing visible light from said point of contact through said probe such that said visible light exits said probe into said anterior chamber along a viewing axis which is generally parallel to said output axis.

7. The method of claim 6, wherein the viewing axis is generally collinear with said output axis.

8. The method of claim 6, additionally comprising viewing said visible light after passing through the probe.

9. The method of claim 5, wherein said viewing step comprises looking through the cornea of the eye.

10. The method of claim 7, additionally comprising the step of using the probe to manipulate the cut portion of the anterior capsule.

11. The method of claim 9, additionally comprising application to said eye of viscoelastic material.

12. The method of claim 2, wherein said light beam has a wavelength in an invisible portion of the optical spectrum.

13. The method of claim 12, wherein said wavelength is 2.94 μm.

14. The method of claim 12, wherein the redirecting step comprises reflecting said light beam at a surface of said probe through total internal reflection, said surface being transparent to visible light.

15. The method of claim 14, wherein said visible light propagates towards said probe generally along said output axis.

16. The method of claim 1, additionally comprising forming a smooth non-serrated capsulotomy margin with said laser light beam.

17. The method of claim 16, additionally comprising phacoemulsification or phacoablation of the lens underlying said anterior capsule.

18. The method of claim 17, wherein said phacoemulsification or phacoablation is performed using laser light from said probe.

19. The method of claim 2, additionally comprising irrigating said tissue with irrigation fluid.

20. The method of claim 19, wherein said irrigation fluid is a balanced salt solution.

21. A method of performing surgery on the eye of a mammal, comprising:

inserting a laser probe into an anterior chamber of said eye;

directing a laser light beam into said laser probe along a longitudinal axis;

redirecting said light beam in said laser probe at a location within said anterior chamber;

directing the redirected light beam along an output axis at an angle relative to said longitudinal axis;

performing an anterior capsulotomy by forming an incision with a smooth, non-serrated capsulotomy margin on the anterior capsule of said eye using said light beam, without significantly emulsifying the lens beneath the portion of the capsule within the margin;

removing the portion of said anterior capsule within said margin to expose the lens therebeneath; and subsequent to the preceding steps, removing the lens of the eye.

22. The method of claim 21, wherein the step of forming an incision comprises forming an incision with a substantially circular capsulotomy margin, and wherein the step of removing the lens comprises emulsifying the lens using laser light at an energy level higher than that used during the step of performing an anterior capsulotomy.

23. The method of claim 21, wherein said probe has a surface inclined at an angle to said axis, said method additionally comprising utilizing said surface to manipulate the portion of said anterior capsule within said margin.

24. The method of claim 21, additionally comprising using said probe to manipulate the portion of said anterior capsule within said margin.

25. The method of claim 21, wherein the redirecting step comprises totally internally reflecting said light beam at a surface of said probe.

26. The method of claim 21, additionally comprising viewing said margin during the forming step by looking through a transparent portion of said probe.

27. The method of claim 21, wherein said light beam is of non-ultraviolet wavelength.

28. The method of claim 21, wherein said light beam is provided as pulses at a frequency greater than 10 Hz.

29. The method of claim 8, wherein said frequency is between 20 Hz and 30 Hz.

30. The method of claim 21, wherein said light beam is of light having a wavelength at an absorbance peak of water.

31. The method of claim 21, wherein said light beam is produced by an Erbium:YAG laser.

32. The method of claim 21, wherein said light beam is produced by a Holmium:YAG laser.

33. The method of claim 21, wherein said light beam is provided as pulses at an energy level equal to or less than 30 mJ/pulse.

34. The method of claim 33, wherein said energy level is between 5 mJ/pulse and 10 mJ/pulse.

35. The method of claim 21, additionally comprising forming an incision in said eye through which said probe is inserted.

36. The method of claim 35, wherein said incision is in the sclera of said eye.

37. The method of claim 2, wherein the step of moving the point of contact along a capsulotomy margin comprises cutting the lens capsule along a capsulotomy margin that is substantially circular.

* * * * *